United States Patent [19]
Sorgente et al.

[11] Patent Number: 5,965,620
[45] Date of Patent: *Oct. 12, 1999

[54] METHODS AND COMPOSITIONS FOR ATP-SENSITIVE K+CHANNEL INHIBITION FOR LOWERING INTRAOCULAR PRESSURE

[75] Inventors: Nino Sorgente, Los Angeles; Charles Bakhit, La Verne, both of Calif.

[73] Assignee: Vide Pharmaceuticals, Los Angeles, Calif.

[*] Notice: This patent is subject to a terminal disclaimer.

[21] Appl. No.: 08/908,870

[22] Filed: Aug. 8, 1997

Related U.S. Application Data

[63] Continuation-in-part of application No. 08/466,162, Jun. 6, 1995, abandoned, which is a continuation of application No. 08/096,799, Jul. 23, 1993, Pat. No. 5,629,345.

[51] Int. Cl.$^6$ ................................................. A61K 31/175
[52] U.S. Cl. ........................................... 514/592; 514/913
[58] Field of Search ..................................... 514/592, 913

[56] References Cited

U.S. PATENT DOCUMENTS

| | | |
|---|---|---|
| 3,916,899 | 11/1975 | Theeuwes et al. . |
| 4,001,132 | 1/1977 | McGuire, Jr. . |
| 4,309,432 | 1/1982 | Tanaka et al. . |
| 4,346,106 | 8/1982 | Sudilovaky . |
| 4,454,151 | 6/1984 | Waterbury . |
| 4,484,921 | 11/1984 | Swanson et al. . |
| 4,526,893 | 7/1985 | Takahashi et al. . |
| 4,542,152 | 9/1985 | Shepard . |
| 4,559,361 | 12/1985 | Oka . |
| 4,582,855 | 4/1986 | Kam et al. . |
| 4,590,202 | 5/1986 | Remy . |
| 4,629,730 | 12/1986 | Clark et al. . |
| 4,634,689 | 1/1987 | Witkowski et al. . |
| 4,636,515 | 1/1987 | Barknecht et al. . |
| 4,642,311 | 2/1987 | Baldwin et al. . |
| 4,644,007 | 2/1987 | York, Jr. . |
| 4,647,590 | 3/1987 | Virno . |
| 4,657,925 | 4/1987 | Horn . |
| 4,661,513 | 4/1987 | Berthold et al. . |
| 4,697,022 | 9/1987 | Leinert . |
| 4,709,996 | 12/1987 | Michelson . |
| 4,722,933 | 2/1988 | Horn . |
| 4,746,676 | 5/1988 | Neiss et al. . |
| 4,749,698 | 6/1988 | Neiss et al. . |
| 4,760,085 | 7/1988 | Bartsch . |
| 4,766,151 | 8/1988 | Leclerc et al. . |
| 4,826,869 | 5/1989 | Muchowaki et al. . |
| 4,847,269 | 7/1989 | Clark et al. . |
| 4,847,289 | 7/1989 | Balwin et al. . |
| 4,871,742 | 10/1989 | Bonne et al. . |
| 4,894,390 | 1/1990 | Hartman et al. . |
| 4,897,412 | 1/1990 | LeClerc et al. . |
| 4,902,696 | 2/1990 | Conway et al. . |
| 4,906,467 | 3/1990 | Schwartzman et al. . |
| 4,914,111 | 4/1990 | Hartman et al . |
| 4,923,877 | 5/1990 | Markov et al. . |
| 4,935,422 | 6/1990 | Patil et al. . |
| 4,975,447 | 12/1990 | Schoenwald et al. . |
| 4,975,448 | 12/1990 | Schoenwald et al. . |
| 4,987,417 | 1/1991 | Patil et al. . |
| 4,990,668 | 2/1991 | Mai et al. . |
| 4,994,464 | 2/1991 | Tolman et al. . |
| 5,003,115 | 3/1991 | Strutz . |
| 5,011,846 | 4/1991 | Gittos et al. . |
| 5,013,837 | 5/1991 | Ward et al. . |
| 5,034,406 | 7/1991 | Gluchowski . |
| 5,039,802 | 8/1991 | Blacklock et al. . |
| 5,049,587 | 9/1991 | Okamoto et al. . |
| 5,061,714 | 10/1991 | Tadokoro et al. . |
| 5,075,323 | 12/1991 | Fain et al. . |
| 5,112,820 | 5/1992 | Ward . |
| 5,134,146 | 7/1992 | Showell et al. . |
| 5,281,599 | 1/1994 | Murphy et al. . |
| 5,312,820 | 5/1994 | Ashton et al. . |

FOREIGN PATENT DOCUMENTS

| | | |
|---|---|---|
| 885496 | 1/1981 | Belgium . |
| 0080779 | 6/1983 | European Pat. Off. . |
| 0086126 | 8/1983 | European Pat. Off. . |
| 0087378 | 8/1983 | European Pat. Off. . |
| 0089037 | 9/1983 | European Pat. Off. . |
| 0090516 | 10/1983 | European Pat. Off. . |
| 0113910 | 7/1984 | European Pat. Off. . |
| 0130109 | 1/1985 | European Pat. Off. . |
| 0132190 | 1/1985 | European Pat. Off. . |
| 0175266 | 3/1986 | European Pat. Off. . |
| 0180994 | 5/1986 | European Pat. Off. . |
| 0189801 | 8/1986 | European Pat. Off. . |
| 0235544 | 9/1987 | European Pat. Off. . |
| 0329903 | 8/1989 | European Pat. Off. . |
| 0338507 | 10/1989 | European Pat. Off. . |
| 0370852 | 5/1990 | European Pat. Off. . |
| 0403158 | 12/1990 | European Pat. Off. . |
| 0403360 | 12/1990 | European Pat. Off. . |
| 0437030 | 7/1991 | European Pat. Off. . |
| 0459568 | 12/1991 | European Pat. Off. . |
| 2585574 | 7/1985 | France . |
| 2593395 | 1/1986 | France . |
| 01-246220 | 10/1989 | Japan . |
| 02-262528 | 10/1990 | Japan . |
| WO 83/00043 | 1/1983 | WIPO . |
| WO 86/00896 | 2/1986 | WIPO . |
| WO 87/03583 | 6/1987 | WIPO . |
| WO 87/03584 | 6/1987 | WIPO . |
| WO 89/10757 | 11/1989 | WIPO . |
| WO 90/02124 | 3/1990 | WIPO . |
| WO 90/06111 | 6/1990 | WIPO . |

OTHER PUBLICATIONS

The Merck Index, Eleventh Edition (1989).
Leibowitz et al., *Surv. Ophthamol.* 24 (Suppl):366–400 (1980).
Leske, *Am. J. Epidemiol.* 118:166–191 (1983).
Minckler et al., *Am. J. Ophthamol.* 104:168–173 (1987).

*Primary Examiner*—Zohreh Fay
*Attorney, Agent, or Firm*—Townsend & Townsend & Crew LLP

[57] ABSTRACT

ATP-sensitive K+ channel modulating compounds are incorporated into ophthalmically acceptable carriers for administration to the eye in order to affect intraocular pressure. Such formulations including compounds which inhibit the channel are particularly suitable for treating glaucoma and other disorders related to elevated intraocular pressure. Such formulation which potentiates the channel are particularly suitable for treating hypotonia and other depressed intraocular pressure conditions.

12 Claims, No Drawings

METHODS AND COMPOSITIONS FOR ATP-SENSITIVE K⁺ CHANNEL INHIBITION FOR LOWERING INTRAOCULAR PRESSURE

The present application is a continuation-in-part of application Ser. No. 08/466,162, filed on Jun. 6, 1995, now abandoned, which was a continuation of application Ser. No. 08/096,799, filed on Jul. 23, 1993, now U.S. Pat. No. 5,629,345, the full disclosures of which are incorporated herein by reference.

BACKGROUND OF THE INVENTION

1. Field of the Invention

The present invention relates generally to compositions and methods for lowering intraocular pressure and more particularly to the administration of inhibitors of ATP-sensitive $K^+$ channel to the eye to lower intraocular pressure for the treatment of glaucoma.

Glaucoma is an ocular disorder that is often manifested as an elevated intraocular pressure. It is presently believed that such elevated pressure results from inadequate transport of the intraocular fluid from the anterior chamber, resulting in a detrimental pressure increase. If left untreated, glaucoma will eventually lead to loss of vision in the affected eye. Current treatment methods include forming small laser penetrations in the eye to release excess pressure, as well as the use of systemic and topical drugs for lowering intraocular pressure. Of particular interest to the present invention, topically applied drugs for the treatment of glaucoma include pilocarpine, a cholinergic; timolol maleate, a β-adrenergic receptor blocking agent; epinephrine, an α- and β-adrenergic receptor agonist; dipivefrin, a pro drug of epinephrine; and demecarium bromide, a cholinesterase inhibitor. While these drugs are generally effective, they can have significant adverse side effects, even when administered topically. Topical administration to the eye results in significant absorption leading to such undesirable systemic effects.

Elevated intraocular pressure can be caused by other conditions as well, such as impaired intraocular fluid transport caused by eye surgery, including surgery for glaucoma. No drugs are presently available for surgical implement of the intraocular fluid outflow.

Below normal intraocular pressure can also be a concern. Such reduced intraocular pressure can be caused by a variety of conditions, such as surgery for glaucoma, retinal detachment, uveitis, and the like. No drugs are presently available for the treatment of low intraocular pressure.

Therefore it would be desirable to provide additional drugs useful for the control of intraocular pressure, particularly for the treatment of glaucoma and other disorders related to elevated intraocular pressure, where such drugs have fewer or reduced side effects when compared to present drugs when topically applied. Drugs for the treatment of surgically induced elevated intraocular pressure as well as low (depressed) intraocular pressure would also be desirable. Such drugs should be safe, relatively non-toxic, and be amenable to incorporation in carriers and vehicles suitable for administration to the eye, either topically, by injection, or by ocular insert. These and other objectives will be met by the methods and compositions of the present invention, as described in more detail hereinafter.

2. Description of the Background Art

Compounds having various channel blocking activities, including inhibition of the ATP-sensitive $K^+$ channel, have shown the ability to lower intraocular pressure, e.g. labetalol (an α- and β-adrenergic blocker; Kogure et al. (1981) Arch. Int. Pharm. Ther. 250:109–122); phentolamine (an α-adrenergic blocker; Belmonte et al. (1987) Invest. Optal. Vis. Sci. 28:1649–1654); and antazoline (an H1-blocker; Krupin et al. (1980) Ophthal. 87:1167–1172). Quinine (a non-selective potassium channel blocker) has been suggested (without supporting data) as lowering intraocular pressure (U.S. Pat. No. 4,895,807 to Cherksey). U.S. Pat. No. 5,312,820, to Ashton suggests the use of certain carbonoy and oxycarbonyl derivatives of biphenylmethylamines for the treatment of hypertension and related disorders such as glaucoma. The Ashton compounds in some instances may contain an—($SO_2$—NH—CO)—substituent group.

French patent application 2 585 574 describes the use of 4-phenyl-1,4-dihdro-pyridines for the treatment of glaucoma. The use of antihypertensive drugs for the treatment of glaucoma is suggested in U.S. Pat. No. 4,749,698 and published European applications 175 266; 180 994; and 235 544. The use of anti-inflammatory drugs for the treatment of glaucoma is suggested in U.S. Pat. No. 4,454,151. The use of potassium channel openers for the treatment of glaucoma is suggested in WO 89/10757. The use of dopamine-responsive agonists for the treatment of glaucoma is suggested in U.S. Pat. Nos. 4,722,933 and 4,657,925. The use of certain receptor agonists for the treatment of glaucoma is suggested in U.S. Pat. No. 5,011,846 and published European applications 329 903; 403 360; and 086 126. The use of tricyclic benzo fused compounds for the treatment of glaucoma is suggested in published European application 090 516. The use of angiotensin II receptor antagonists for the treatment of glaucoma is suggested in published European application 403 158. The use of inhibitors of angiotensin-converting enzyme (ACE) inhibitors for the treatment of glaucoma is suggested in U.S. Pat. No. 4,634,689 and WO 86/00896. The use of α2 antagonists for the treatment of glaucoma is suggested in U.S. Pat. No. 4,590,202 and published European application 080 779. The use of β-blockers for the treatment of glaucoma is suggested in U.S. Pat. Nos. 5,003,115; 4,897,412; 4,935,422; 4,661,513; 4,647,590; 5,061,714; 4,990,668; 4,760,085; 4,766,151; 4,642,311; 4,582,855; 4,994,464; 4,897,417; 4,697,022; 4,526,893; published European applications 089 037; 437 030; 113 910; 087 378; and published PCT applications WO 87/03583; 87/03584; 83/00043. The use of carbonic anhydrase inhibitors for the treatment of glaucoma is suggested in U.S. Pat. Nos. 4,975,447; 4,914,111; 4,636,515; 4,975,448; 4,542,152; 5,039,802; 4,847,289; 4,894,390; and published European application 130 109. Other compositions and methods for treating glaucoma are described in U.S. Pat. Nos. 5,112,820; 4,871,742; 4,923,877; 4,346,106; 4,746,676; 5,134,146; 4,826,869; 5,075,323; 4,309,432; 4,906,467; 5,049,587; 5,013,837; 4,902,696; 4,559,361; 4,644,007; 5,034,406; 4,847,269; 4,001,132; 4,629,730; 459 568; Published PCT applications WO/06111; WO 90/02124; European patent publications 370 852; 132 190; 189 801; 338 507; Japanese patent publications 1-246220; 2-262518; French patent publication 2 593 395; Belgian patent publication 885.496.

EP 467 710 suggests that ATP-sensitive potassium channel blockers, such as sulfonyl urea and quinine, may be used to treat Parkinson's disease. EP 171 331 teaches quinine compositions. EP 467 709 (equivalent to U.S. Pat. No. 5,281,599) teaches the use of sulfonyl urea compounds for the treatment of Parkinson's disease. GB 2 177 913 teaches quinine compositions. WO 94/02142 teaches compositions including a sulfonyl urea moiety for treating hypertension.

SUMMARY OF THE INVENTION

Novel methods and compositions for modulating, including both lowering and increasing, intraocular pressure in the eye of a patient have been discovered. The compositions comprise at least one compound which is selective for inhibiting the ATP-sensitive $K^+$ channel present in an ophthalmically acceptable carrier in an amount effective to lower intraocular pressure when administered to an eye having elevated intraocular pressure. By "selective," it is meant that the compounds display substantially diminished or no reactivity with non-ATP sensative potassium and other channels, particularly calcium channels. The ATP-sensitive $K^+$ channel selective inhibiting compounds are preferably sulfonylurea compounds, more preferably being selected from the group consisting of glybenclamide, glipizide, tolbutamide, and tolazamide, and therapeutically equivalent salts and derivatives thereof, and are preferably present in the compositions in concentrations from about 0.1% to 5 % by weight. Non-sulfanyl urea compounds, however, have also been found to be effective, such as 2, 3-butanedione and 5-hydroxydecanoic acid. Particular formulations include those suitable for topical application, for injection, and for combination in an ocular insert.

Compositions according to the present invention further comprise at least one ATP-sensitive $K^+$ channel potentiating compound, i.e., $K^+$ channel opener, such as diazoxide. Such compositions are used for increasing intraocular pressure in treatment of reduced intraocular pressure condition.

Methods according to the present invention comprise administering such compositions directly to the eye in an amount effective to lower the intraocular pressure. Suitable administration methods include topical application, injection, and timed release using an ocular insert or equivalent formulation.

The methods and compositions of the present invention are particularly useful for the treatment of glaucoma, and overcome many of the limitations of prior glaucoma treatment methods and compositions.

DESCRIPTION OF THE PREFERRED EMBODIMENT

The methods and compositions of the present invention are intended for treatment of glaucoma and other conditions which manifest elevated intraocular pressure in the eye of a patient, particularly human patients, but including other mammalian hosts. Glaucoma is a term which embraces a group of ocular diseases characterized by elevated intraocular pressure levels which can damage the eye. Elevated intraocular pressures often exceed 20 mmHg and it is desirable that such elevated pressures be lowered to below 18 mmHg. In the case of low-tension glaucoma, it is desirable that the intraocular pressure be lowered below that exhibited by the patient prior to treatment. Glaucoma diseases are well-described in the medical literature. See, e.g., Leibowitz et al. (1980) Surv. Ophthalmol. 24 (Suppl.) :366–400 and Leske (1983) Am. J. Epidemiol. 118:166–191. Other conditions which result in elevated intraocular pressure levels include cataract surgery, steroid treatment, and treatment with other drugs known to cause intraocular pressure. The methods and compositions of the present invention are intended to treat all such conditions, preferably in order to lower the intraocular pressure to a manageable level as described above.

Intraocular pressure can be measured by conventional tonometry techniques. A particularly convenient method for measuring intraocular pressure is the use of the Tono-Pen as described in Minckler et al. (1987) Am. J. Ophthamol. 104:168–173.

The methods and compositions of the present invention are also intended for treatment of hypotonia and/or reduced intraocular pressure conditions of the eye. Reduced intraocular pressures are generally considered below about 8 mmHg. Such conditions may result from a variety of causes, such as surgery for glaucoma, retinal detachment, uveitis, and the like.

The methods and compositions of the present invention rely on administering compounds which specifically modulate, i.e. inhibit or potentiate the ATP-sensitive $K^+$ channel compounds directly to the eye of the patient or host. Suitable ATP-sensitive $K^+$ channel inhibiting compounds useful for the treatment of elevated intraocular pressure conditions include sulfonyl urea compounds, such as glybenclamide, glipizide, tolbutamide, and tolazamide, as well as non-sulfonyl urea compounds, such as 2, 3-butanedione and 5-hydroxyderanoic acid, and therapeutically equivalent salts and derivatives thereof. Each of these compounds is described in the Merck Index, 10th Edition, with suitable source information provided). Suitable ATP-sensitive $K^+$ channel potentiating (increasing) compounds useful for the treatment of hypotonia and reduced intraocular pressure conditions include diazoxide and therapeutically equivalent salts and derivatives thereof.

The ATP-sensitive $K^+$ channel is one of the approximately 15 $K^+$ channels that have been identified. The ATP-sensitive $K^+$ channel is regulated by intracellular ATP such that it is spontaneously active in the absence of ATP and closed by increasing ATP concentration in the cytoplasmic side of the membrane. The ATP-sensitive $K^+$ channel is not activated by intraocular $Ca^{+2}$, and gating of the channel is independent of membrane potential. The channel is selective for $K^+$, and it is selectively inhibited by sulfonylurea compounds, such as glybenclamide, glipizide, tolbutamide, and tolazamide, and the like. Compounds useful in the present invention will specifically modulate the ATP-sensitive $K^+$ channel and will display no substantial activity with respect to the other known potassium channels or to calcium channels. It is expected that other selective ATP-sensitive $K^+$ channel inhibitors will be identified in the future and that they will be useful in the methods of the present invention. ATP-sensitive $K^+$ channels have been identified in cardiac cells, skeletal and smooth muscle, neurons and pancreatic $\beta$-cells. It is very likely that ATP-sensitive $K^+$ channels are found in many cells, and the data present in the Experimental section hereinafter indicate existence of such a channel in the eye. Thus, a decrease in intraocular pressure occurs when the eye is treated with selective inhibitors of the ATP-sensitive $K^+$ channel and an increase in intraocular pressure occurs when the eye is treated with a $K^+$ channel opener.

ATP-sensitive $K^+$ channel inhibitors and potentiators useful in the present invention will display at least a 3-fold selectively for the ATP-sensitive $K^+$ channel relative to other potassium channels, calcium channels, and sodium channels, preferably displaying at least 5-fold selectivlity, more preferably at least 10-fold selectivity, still more preferably at least 100-fold selectivity, and often higher selectivities. Such selectivity thresholds can be measured by determining the relative amounts of a modulating compound which are required to achieve a 50% inhibition or 100% potentiation of the ATP-sensitive $K^+$ channel and the ohter channel(s). The other channels should require at least 3-fild greater amounts of the compound to achieve the same level of inhibition or potentiation.

According to the present invention, such ATP-sensitive $K^+$ channel modulating compounds will be incorporated into compositions suitable for direct administration to a patient's eye. By "direct administration," it is meant that the compounds will be applied topically, or by injection or instillation, into the eye. Such direct administration does not include systemic forms of administration, such as oral or parenteral administration, e.g., intramuscular, subcutaneous, or intraperitoneal injection. Direct administration of the ATP-sensitive K⁺ channel modulating compounds is intended to introduce the compounds directly into the eye so that they will be transported into the anterior chamber where the compounds will be effective to lower intraocular pressure, most likely by enhancing the transport or release of intraocular fluid from the anterior chamber or by decreasing fluid production.

The ATP-sensitive K⁺ channel inhibiting compounds will be administered to the eye in amounts and over a schedule effective to lower the intraocular pressure of the eye, particularly when the intraocular pressure was previously elevated, i.e., above about 18 mmHg, usually above 20 mmHg, or when damage to the optic nerve is noted. The amount of the compound required for such lowering will depend on a number of factors, including degree of initial pressure elevation, condition of the patient, activity of the particular compound which is being administered, and the like, with exemplary amounts typically being in the range from about 50 μg to 5 mg per dose (i.e., single application of the composition), usually being from 250 μg to 1 mg per dose.

The ATP-sensitive K⁺ channel potentiating compounds will be administered to the eye in amounts and over a schedule effective to raise the intraocular pressure of the eye, particularly when the intraocular pressure was previous reduced or depressed, i.e. below about 20 mmHg, usually below 18 mmHg, and more usually below 8 mmHg, or when the eye suffers from hypotonia for any reason. The amount of the compound required for such pressure increase and/or hypotonia alleviation will depend on a number of factors, including the initial pressure, condition of the pertinent activity of the administered compound, and the like, with exemplary amounts typically being in the range from about 50 μg to 5 mg per dose (i.e., single application of the composition) usually being from 250 μg to 1 mg per dose.

Such dosages may be conveniently achieved using compositions having the compound present in a suitable ophthalmically acceptable carrier at a concentration in the range from about 0.1 weight percent to 5 weight percent. Concentrations above 5 weight percent are potentially toxic and should generally be avoided. Specific formulations will be described in greater detail hereinafter.

It will also be possible to incorporate the ATP-sensitive K⁺ channel modulating compounds of the present invention into controlled-release formulations and articles, where the total amount of compound is released over time, e.g., over a number of minutes or hours. Typically, the total dosage of the compound will be within the limits described above for non-controlled-release formulations, but in some cases may be greater, particularly when the controlled release formulations act over relatively longer periods of time. Suitable controlled release articles for use with the compositions of the present invention include solid ocular inserts available from commercial vendors such as Alza Corporation, Palo Alto, Calif. (sold under the Ocusert® trade name) and from Oculex Corporation, Palo Alto, Calif.

Other controlled-release formulations may be based on polymeric carriers, including both water-soluble polymers and porous polymers having desirable controlled-release characteristics. Particularly suitable polymeric carriers include various cellulose derivatives, such as methylcellulose, sodium carboxymethylcellulose, hydroxyethylcellulose, and the like. Suitable porous polymeric carriers can be formed as polymers and copolymers of acrylic acid, polyacrylic acids, ethylacrylates, methylmethacrylates, polyacrylamides, and the like. Certain natural biopolymers may also find use, such as gelatins, alginates, pectins, agars, starches, and the like. A wide variety of controlled-release carriers are known in the art and available for use with the present invention.

Topical compositions for delivering the ATP-sensitive K⁺ channel modulating compounds of the present invention will typically comprise the compound present in a suitable ophthalmically acceptable carrier, including both organic and inorganic carriers. Exemplary ophthalmically acceptable carriers include water, buffered aqueous solutions, isotonic mixtures of water and water-immiscible solvents, such as alkanols, arylalkanols, vegetable oils, polyalkalene glycols, petroleum-based jellies, ethyl cellulose, ethyl oleate, carboxymethylcelluloses, polyvinylpyrrolidones, isopropyl myristates, and the like. Suitable buffers include sodium chloride, sodium borate, sodium acetate, gluconates, phosphates, and the like.

The formulations of the present invention may also contain ophthalmically acceptable auxiliary components, such as emulsifiers, preservatives, wetting agents, thixotropic agents (e.g., polyethylene glycols, antimicrobials, chelating agents, and the like). Particularly suitable antimicrobial agents include quaternary ammonium compounds, benzalkonium chloride, phenylmercuric salts, thimerosal, methyl paraben, propyl paraben, benzyl alcohol, phenylethanol, sorbitan monolaurate, triethanolamine oleate, polyoxyethylene sorbitan monopalmitylate, dioctyl sodium sulfosuccinate, monothioglycerol, and the like. Ethylenediamine tetracetic acid (EDTA) is a suitable chelating agent.

The following formulations are exemplary of the compositions of this invention. These formulations are illustrative only and are not intended to limit the scope of this invention and should not be so construed.

FORMULA 1

A sterile solution for topically treating glaucoma or reducing intraocular pressure and which is well tolerated by the eye is prepared as follows:

| Component | Amount |
| --- | --- |
| Glybenclamide | 100 μg to 20 mg |
| Sodium chloride | 8 mg |
| Boric acid | 1 mg |
| Benzalkonium chloride | 0.1 mg |
| Hydrochloric acid/sodium hydroxide | pH 7.0 |
| Water for injection (qs) | 1 ml |

FORMULA 2

A sterile solution for topical treatment of the eye to increase intraocular pressure is prepared as described in Formula 1 except that diazoxide is used in place of glybenclamide.

FORMULA 3

An injectable solution for use in treating glaucoma or reducing intraocular pressure is prepared as follows:

| Component | Amount |
| --- | --- |
| Glybenclamide | 100 µg to 20 mg |
| Methyl paraben | 1 mg |
| Propyl paraben | 1 mg |
| Sodium chloride | 5 mg |
| Water for injection (qs) | 1 ml |

FORMULA 4

A sterile injectable solution for increasing intraocular pressure is prepared as described in Formula 3 except that diazoxide is used in place of glybenclamide.

The following examples are offered by way of illustration, not by way of limitation.

EXPERIMENTAL

Formulations of inhibitors of ATP-sensitive $K^+$ channels (Table 1) were tested for their ability to decrease intraocular pressure in normal rabbits. Diazoxide, a $K^+$ channel opener, was tested for its ability to raise intraocular pressure in normal rabbits. Formulations were prepare in NaCl/borate buffer (0.8 mg NaCl, 1.0 mg boric acid, pH 7.2, water to 1 ml) and tested as follows: Seventy New Zealand white rabbits were divided into seven groups; 25 were treated with vehicle; 20 were treated with timolal; 10 were treated with glybenclamide; 5 with tolazamide; 10 with tolbutamide; 5 with chlorpropamide, and 5 with diazoxide. Each animal received 80 µl of solution in two doses, 40 µl each, at an interval of two minutes. Intraocular pressure was determined with a Tono-Pen before administration ("0" time), at one and two hours following administration. The results are set for in Table 1.

TABLE 1

| | Intraocular Pressure[2] | | |
| --- | --- | --- | --- |
| Formulation[1] | 0 hr | 1 hr | 2 hr |
| Vehicle | 100 | 100 | 100 |
| 1% Glybenclamide | 100 | 92 | 97 |
| 1% Tolazamide | 100 | 86 | 93 |
| 1% Tolbutamide | 100 | 84 | 94 |
| 1% Chlorpropamide | 100 | 92 | 98 |
| 1% Diazoxide | 100 | 129 | 123 |

[1]weight percent of each compound
[2]percent initial pressure

The results presented in TABLE 1 clearly show that inhibitors of ATP-sensitive $K^+$ channels lower intraocular pressure. Of the four sulfonylureas, which are selective inhibitors of ATP-sensitive $K^+$ channels, tolbutamide and tolazamide appear to be more effective than glybenclamide or chlorpropamide. However, since these compounds are insoluble in aqueous solutions, the activity of these compounds in lowering intraocular pressure may be very different if they are administered in a vehicle in which they are soluble. Since the sulfonylureas which are selective inhibitors of the ATP-sensitive $K^+$ channels lower intraocular pressure, and since diazoxide, which is a $K^+$ channel opener, increases intraocular pressure, it appears that intraocular pressure is at least in part dependent on the ratio of intracellular to extracellular potassium.

Similar tests were performed with 2, 3-butanedione and 5-hydroxydecanoic acid, both of which are specific non-sulfonyl urea inhibitors of the ATP-sensative $K^+$ channel. The results are shown in TABLE 2.

TABLE 2

| | Intraocular Pressure | | |
| --- | --- | --- | --- |
| Formulation | 0 hr | 1 hr | 2 hr |
| 2,3-butanedione | 100 | 87 | 88 |
| 5-hydroxdecanoic acid | 100 | 83 | 87 |

The results demonstrate that the ability to lower intraocular pressure is possessed by both sulfonyl urea and non-sulfonyl urea ATP-sensitive $K^+$ channel inhibitors.

Although the foregoing invention has been described in some detail by way of illustration and example, for purposes of clarity of understanding, it will be obvious that certain changes and modifications may be practiced within the scope of the appended claims.

What is claimed is:

1. A method for affecting intraocular pressure in an eye of a patient, said method comprising administering to the eye a compound which specifically modulates the ATP-sensitive $K^+$ channel present in an ophthalmically acceptable carrier in an amount effective to change said intraocular pressure.

2. A method as in claim 1, wherein the compound is administered by topical application to the eye.

3. A method as in claim 1, wherein the compound is administered by injection into the anterior chamber.

4. A method as in claim 1, wherein the compound is administered using an ocular insert.

5. A method as in claim 1, wherein the ATPase compound is an ATP-sensitive $K^+$ channel inhibitor, whereby intraocular pressure is decreased.

6. A method as in claim 5, wherein the compound is selected for the group consisting of glybenclamide, glipizide, tolbutamide, and tolazamide, chlorpropamide or other sulfonylureas, 2,3-butanedione, 5-hydroxdecanoic acid, and therapeutically equivalent salts or derivatives thereof.

7. A method as in claim 5, wherein the patient suffers from glaucoma.

8. A method as in claim 1, wherein the compound is an ATP-sensitive $K^+$ channel potentiator, whereby an intraocular pressure is increased.

9. A method as in claim 8, wherein the compound is diazoxide or a therapeutically equivalent salt or derivative thereof.

10. A method as in claim 7, wherein the patient suffers from hypotonia.

11. A method as in claim 1, wherein the compound is administered in single dosages having from 50 µg to 2 mg of the compound per dosage.

12. A method as in claim 11, wherein the dosages are administered from 1 to 4 times per day.

* * * * *